US006995239B1

(12) United States Patent
Dunn-Coleman et al.

(10) Patent No.: US 6,995,239 B1
(45) Date of Patent: Feb. 7, 2006

(54) HYPHAL GROWTH IN FUNGI

(75) Inventors: Nigel Dunn-Coleman, Los Gatos, CA (US); Geoffrey Turner, Fulwood (GB); Sarah E. Pollerman, Yorkshire (GB); Stephen D. Memmott, Lincoln, NE (US)

(73) Assignees: Genencor International, Inc., Palo Alto, CA (US); University of Sheffield, Sheffield (GB)

(*) Notice: Subject to any disclaimer, the term of this patent is extended or adjusted under 35 U.S.C. 154(b) by 0 days.

(21) Appl. No.: 09/275,549

(22) Filed: Mar. 24, 1999

(51) Int. Cl.
C07K 14/38 (2006.01)

(52) U.S. Cl. .......................... 530/350; 435/6; 435/69.1

(58) Field of Classification Search ................. 530/350; 435/6, 69.1
See application file for complete search history.

(56) References Cited

FOREIGN PATENT DOCUMENTS

WO    WO 97/26330    7/1997

OTHER PUBLICATIONS

Copy of International Search Report for PCT/US 00/07615.
Erjavec, Z. et al., "Applicability of random primer R143 for determination of *Aspergillus fumigatus* DNA ", Journal of Medical and Veterinary Mycology, vol. 35, No. 6, Nov. 1997, pp. 399–403, XP-000929979.
Erjavec, Z. et al., "*Aspergillus fumigatus* putative vacuolar protein sorting homolog gene, partial cds.", Database EMBL 'Online! Accession AF004837, Jun. 28, 1997, XP-002144970.
Kupfer, D. et al., "xlf08al. rl *Aspergillus nidulans* 24 hr asexual development and vegetative cDNA lambda zap library *Emericella nidulans* cDNA clone Xlf08al 5', mRNA sequence", Database EMBL 'Online! Accession Al212286, Oct. 20, 1998 XP-002144971.
Kupfer, D. et al., "e4b02al. rl Aspergillus nidulans 24 hr asexual development and vegetative cDNA lambda zap library Emericella nidulans cDNA clone e4b02al 5', mRNA sequence" , Database EMBL 'Online!Accession AA784458, Feb. 8, 1998, XP-002144972.
Memmott, S. et al., Abstract of Poster 339. "Morphological and genetic characterization of Hbr-2, a hyperbranching mutant of *Aspergillus nidulans*", 20th Fungal Genetics Conference, 'Online! Mar. 24–29, 1999, XP-002144968.
Yarden, O. et al., "cot–1, a gene required for hyphal elongation in *Neurospora crassa*, encodes a protein kinase", EMBO Journal, vol. 11, No. 6, 1992, pp. 2159–2166, XP-002144969.
McGoldrick, C.A. et al., "myoA of *Aspergillus nidulans* encodes an essential myosin I required for secretion and polarized growth", The Journal of Cell Biology, vol. 128, No. 4, Feb. 1, 1995, pp. 577–587, XP-000530233.
Ausubel, Frederick et al., "Short Protocols in Molecular Biology," *Current Protocols in Molecular Biology, Chapter 9*, Greene Publishing Associates & John Wiley & Sons, Inc. 1987.
Benton et al., "Steering λgt Recombinant Clones by Hybridization to Single Plaques in situ," *Science*, vol. 196, No. 4286, pp. 180–182, Apr. 8, 1977.
*Berger and Kimmel, "Guide to Molecular Cloning Techniques," *Methods in Enzymology*, Academic Press, San Diego, CA, vol. 152, 1987.
Carlile, M., "The Success of the Hypha and Mycelium," The Growing Fungus, ed. Gow. N. A. R. & Gadd, G. M., Chapman & Hall, pp. 3–19.
*Coombs, J., *Dictionary of Biotechnology*, Stockton Press, New York, N.Y., 1994.
*Dieffenbach et al., *PCR Primer, a Laboratory Manual*, Cold Springs Harbor Press, Plainview, N.Y., 1995.
Finkelstein, D., "Transformation," *The Biotechnology of Filamentous Fungi*, pp. 113–156, Eds, D.B. Finkelstein and C. Ball, Boston, Butterworth–Heinemann, 1992.
Fungaro et al., "Transformation of *Aspergillus nidulans* by microprojectile bombardment on intact conidia," *FEMS Microbiology Letters*, 125:293–298 (1995).
*Glover, D. M. ed., *DNA Cloning: A Practical Approach*, MRL Press, Ltd., Oxford, U.K., vol. I, II.
Grindley et al., "Conversion of Glucose to 2–Keto–L–Gulonate, an Intermediate in L–Ascorbate Synthesis, by a Recombinant Strain of *Erwinia citreus*," *Applied and Environmental Microbiology*, vol. 54, No. 7, Jul. 1988, pp. 1770–1775.
De Groot, et al., "*Agrobacterium tumefaciens*–mediated transformation of filamentous fungi," *Nature Biotechnology*, vol. 16, 1998, pp. 839–842.
Grunstein et al., "Colony hybridization: A method for the isolation of cloned DNAs that contain a specific gene," *Proc. Nat. Acad. Sci. USA*, vol. 72, No. 10, pp. 3961–3965, Oct., 1975.
Hein, Jotun, "Unified Approach to Alignment and Phylogenies," *Method in Enzymology*, 183:626–645 (1990).
Higgins et al., "Fast and sensitive multiple sequence alignments on microcomputer," *CABIOS*, vol. 5, 1989, p. 151–153.
Martinelli & J. R. Kinghorn, "*Aspergillus*: 50 Years On," (1994) vol. 29, ed S. D., pp. 33–58.
Martinelli & J. R. Kinghorn, "*Aspergillus*: 50 Years On," (1994) vol. 29, ed S. D., pp. 561–602.
Pearson et al., "Improved tools for biological sequence comparison," Proc. Natl. Acad. Sci. USA, vol. 85, pp. 2444–2448, Apr. 1988.
* Sambrook, J. et al., Molecular Cloning: A Laboratory Manual, $2^{nd}$ ed., Cold Spring Harbor Laboratory Press, Cold Spring Harbor, New York, 1989.

*Primary Examiner*—James Ketter
(74) *Attorney, Agent, or Firm*—Genencor International, Inc.

(57) ABSTRACT

The present invention provides a method for producing desired proteins or chemicals in fungal host cells which comprise modulating the nucleic acid encoding proteins associated with hyphal growth. The amino acid and nucleic acid sequence of hbrA is provided.

1 Claim, 9 Drawing Sheets

```
                    10                    30                    50
GATCACCAGGAATTGCGTTGCCTGATGCATGGTTGGGAGGGCCGCCGAGGTCCACGCCAG
                    70                    90                   110
GTGGTGGGGGTGCTATACCGTGCTGCGCTTTTGCCCTCGTGTAAGGGTCAGCAGGAATCG
                   130                   150                   170
GTTTCGCGTAAGGATTCGCTTCGGCAGGAGGGCTCTTGTTCTTCGACCTCGATCCAAAGA
                   190                   210                   230
GGGCGCGGCGGTTGGAGGAATCGTCGTCGCCGGCGTCTGACGACTTTTGAGGCCGAATC
                   250                   270                   290
GCTTCATAGCGTATTTTAGCTAGAATACTTCGCCGAAAcCAGCGTAGGAATAtTAGAGTG
                   310                   330                   350
AAAATAATAAATTGAGAGGCTATTTATGATTGACTGAGAATTGAAGAGAGGGGAAGGGAA
                   370                   390                   410
GGAGGGAGGGGAGCGAAGATGTTAAGTGTCAGGGGAGCAGCAGCGGCAAAAGTGTCAAGA
                   430                   450                   470
CGCTCCTGAGACTCAAAGGCAGCTATGTAATCATGATACACATAGTTGTGCTGCAATTCT
                   490                   510                   530
GGCTATCAGTGAGTATTTTACCGTATGATTACTCACCAATTCGACTCCACTAAGCCGAAA
                   550                   570                   590
GAAGCTAGCGGGGATGGCTGGACCCTTCTAAGCCTCAACTGAGGGCGGTGCCGCAGTCAA
                   610                   630                   650
ACGTCAACTGCTCCCACCCCATGCTTCGTATAAGGTAGCCATGGCACCATTCCCTGGGTC
                   670                   690                   710
TGATGCCGACAATATCAAGGACAAGGCCCGTAAAGGCTTGCTGAATCTTCTCGAAGGCGT
```

FIG._1A

```
              730              750              770
              .                .                .
GAGTAAGGCTCCTAGTTGGCACTGTTTCTGGTTCTAGCCTGATTCATTACCTCGATCTAG 790              810              830
              .                .                .
GTCCGTGGGAAGAAGAACCTGGTGATTAGCCAGGGGCTTGCTGGGCCCGTCGGGCTTTTT 850              870              890
              .                .                .
GTCAAGTTTTCGCAGCTTCAGGAGTATGGCGTAGACCGGGTATTCTTGCTTGAAAATGGA 910              930              950
              .                .                .
AATGTCGACTCTTCTCAGCGCAATGTGGTATTTCTAGCGTACGCCGAAAAGATCCGCCAG 970              990              1010
              .                .                .
GTGCGGGCAGTGGCAGGTATGTCATGATCTTTATCCACCTTTGATTTACATACCCAAATG 1030             1050             1070
              .                .                .
ACTGTAAATGCGAAGGCTCCTTGCTATCGCGCTTGCTGGGAGCATTAAAGTTACGCAGAC 1090             1110             1130
              .                .                .
TTCTTCTCCACTCTGCGTAATCAGTCAAGCTCCCTATATTGAAACTTCGTTTAGCAGCTT 1150             1170             1190
              .                .                .
ATCCCTAAGGCTTTCTTTCTCTGCCTCGTATGACTGAATGCCATCAGAATAAGCTGACAA 1210             1230             1250
              .                .                .
GTTTTACAGAGCAGATCCAAAGGCTTCAACGCAACAGCAGTATAGACCATGAATTTTCCA
                                                  H  E  F  S  I 1270             1290             1310
              .                .                .
TCTTTTGGGTTCCAAGACGGACCCTCGTAAGCAATAACATCCTAGAGAGCGCAGGCATCA
   F  W  V  P  R  R  T  L  V  S  N  N  I  L  E  S  A  G  I  I 1330             1350             1370
              .                .                .
TTGGAGATGTGAGCATCGCTGAGCTGCCTCTTTACTTTTTTCCTCTAGAGCAGGACGTTC
   G  D  V  S  I  A  E  L  P  L  Y  F  F  P  L  E  Q  D  V  L
```

*FIG._1B*

```
       1390                1410                1430
         .                   .                   .
TTTCTTTGGAACTGGATGACTCTTTTGCGGACTTGTACCTGGTGAGATCTTTCTCCTGGA
  S  L  E  L  D  D  S  F  A  D  L  Y  L 1450                1470                1490
         .                   .                   .
GATAGTGATCAGTGCTGATTCATTTTGTAGCACAAGGAtccTGGGTGCATCTTCCATTCC
                             H  K  D  P  G  C  I  F  H  S 1510                1530                1550
         .                   .                   .
GCAAAGGCTCTTATGgctATTCAACAGAGACATGGCTATTTTCCTCGGATAGTAGGCAAA
 A  K  A  L  M  A  I  Q  Q  R  H  G  Y  F  P  R  I  V  G  K 1570                1590                1610
         .                   .                   .
GGCGATCATGCTCGACGACTCGCTGACCTCCTGCTGCGGATGAGGAAGGAGATTGACGCA
 G  D  H  A  R  R  L  A  D  L  L  L  R  M  R  K  E  I  D  A 1630                1650                1670
         .                   .                   .
GAGGAAAGCTCAGGACTGACAGGACTGTCTTTCCGGGGACTTTTACCCAGCTCAAGCATT
 E  E  S  S  G  L  T  G  L  S  F  R  G  L  L  P  S  S  I 1690                1710                1730
         .                   .                   .
GAGAGTTTGATCATCATTGACCGAGAGGTGGACTTCGGCACCCCTCTGCTTACACAGCTA
 E  S  L  I  I  I  D  R  E  V  D  F  G  T  P  L  L  T  Q  L 1750                1770                1790
         .                   .                   .
ACGTATGAGGGTCTCATCGATGAGTTGGTAGGAATCAAGCACAACCAAGCGGACATTGAT
 T  Y  E  G  L  I  D  E  L  V  G  I  K  H  N  Q  A  D  I  D 1810                1830                1850
         .                   .                   .
ACGACAATTGCAGGGGCCAGCTCAACTCCCCAGGCCCAGGAGTCTTCCAAAGCATCTCAA
 T  T  I  A  G  A  S  S  T  P  Q  A  Q  E  S  S  K  A  S  Q 1870                1890                1910
         .                   .                   .
CAGGCTAAGCAAGGTCAAAAGCGGAAGATTCAGTTGGATTCGTCTGACCAACTGTTCAGT
 Q  A  K  Q  G  Q  K  R  K  I  Q  L  D  S  S  D  Q  L  F  S
```

FIG._1C

```
              1930                1950                1970
                .                   .                   .
CAACTCCGTGACGCGAATTTTGCTATAGTCGGCGATATCCTGAATAAGGTAGCACGTCGA
 Q  L  R  D  A  N  F  A  I  V  G  D  I  L  N  K  V  A  R  R 1990                2010                2030
                .                   .                   .
TTAGAAACAGATTATGAGAGCCGTCATACAGCAAAAACGACAACTGAACTTCGCGAGTTT
 L  E  T  D  Y  E  S  R  H  T  A  K  T  T  E  L  R  E  F 2050                2070                2090
                .                   .                   .
GTGAATAAACTACCATCATATCAACTCGAACATCAAAGCTTGAGAGTTCACACCAACCTC
 V  N  K  L  P  S  Y  Q  L  E  H  Q  S  L  R  V  H  T  N  L 2110                2130                2150
                .                   .                   .
GCTGAGGAAATCATGAAAAACACGCGCTCAGACACTTTCCGCAAGATCCTCGAAGTGCAA
 A  E  E  I  M  K  N  T  R  S  D  T  F  R  K  I  L  E  V  Q 2170                2190                2210
                .                   .                   .
CAGAACGACGCTGCAGGCGCCGACCCAACTTACCAACATCCTCTCATTGAGGAACTCATC
 Q  N  D  A  A  G  A  D  P  T  Y  Q  H  P  L  I  E  E  L  I 2230                2250                2270
                .                   .                   .
GCCCGGGATATTCCACTGAAGACAATCCTCCGTTTGCTTTGTCTCGAATCATGCATGTCC
 A  R  D  I  P  L  K  T  I  L  R  L  L  C  L  E  S  C  M  S 2290                2310                2330
                .                   .                   .
GGTGGCCTACGGCCTAAAGACCTCGAGAGTTTTAAACGCCAAGTCGTCCACGCATACGGG
 G  G  L  R  P  K  D  L  E  S  F  K  R  Q  V  V  H  A  Y  G 2350                2370                2390
                .                   .                   .
CACCAACACCTGCTAACATTCAGTGCTTTGGAGAAGATGGAGCTTCTCCAGCCCCGGTCG
 H  Q  H  L  L  T  F  S  A  L  E  K  M  E  L  L  Q  P  R  S 2410                2430                2450
                .                   .                   .
TCTGCAACCACAATGCTAATTCCCGGCACGGGCACCCAAACGGGATCGAAAACAAACTAC
 S  A  T  T  M  L  I  P  G  T  G  T  Q  T  G  S  K  T  N  Y
```

FIG._1D

```
            2470                  2490                 2510
              .                    .                    .
GCCTACTTTCGCAAAAATCTTCGCCTGGTCGTCGAAGAAGTTAGCGAGAAGGAACCTGAA
 A  Y  F  R  K  N  L  R  L  V  V  E  E  V  S  E  K  P  E 2530                  2550                 2570
              .                    .                    .
GATATCGCTTATGTCTACAGCGGTTTCGCCCCTCTCAGCATTCGCCTTGTGCAGTGCGTC
 D  I  A  Y  V  Y  S  G  F  A  P  L  S  I  R  L  V  Q  C  V 2590                  2610                 2630
              .                    .                    .
TTGCAGAAATCATACGTCATGTCGCTTATGAAAGGTGGCCCGGCTGCGCACGCGAATACC
 L  Q  K  S  Y  V  M  S  L  M  K  G  G  P  A  A  H  A  N  T 2650                  2670                 2690
              .                    .                    .
GCATCCCCAGGCTGGCTTGGATATGAAGATGTGGTGAAGAGTGCGCGTGGATCGACGTTC
 A  S  P  G  W  L  G  Y  E  D  V  V  K  S  A  R  G  S  T  F 2710                  2730                 2750
              .                    .                    .
AGTATTGTCCAAAAGGGCGACGATAAAGCGGTTCGTGCGCGGCAGACACTGAGTGGTAAC
 S  I  V  Q  K  G  D  D  K  A  V  R  A  R  Q  T  L  S  G  N 2770                  2790                 2810
              .                    .                    .
AATGCGGCTAAGACCGTGTATGTGTTCTTCCTCGGAGGGATCACATTTACGGAAATCGCG
 N  A  A  K  T  V  Y  V  F  F  L  G  G  I  T  F  T  E  I  A 2830                  2850                 2870
              .                    .                    .
GCATTGCGGTTCATTGCGGCACAGGAGGCGCCGAGGCGGAACATTGTGATTTGTACTACG
 A  L  R  F  I  A  A  Q  E  A  P  R  R  N  I  V  I  C  T  T 2890                  2910                 2930
              .                    .                    .
GGAATCATTAATGGAGATCGGATGATGGATGCTGCGCTTGAGAAGGGGGGGTTTGCCTTG
 G  I  I  N  G  D  R  M  M  D  A  A  L  E  K  G  G  F  A  L 2950                  2970                 2990
              .                    .                    .
ACTGAGTCTTGACCTCGTAGAGCGTACAGTTAATGTCATAGGAACTATACCGCTATCCAT
 T  E  S
```

| | | | | | | |
|---|---|---|---|---|---|---|
| hbra | GLIDELVGIK | HNQADIDTTI | AGASSTPQAQ | ESSKASQQA. | KQGQKRKIQL | D.SSDQLFSQ | 209 |
| afvac | GLIDEFVGIK | NNQADVDTAI | VGANSVPQAQ | ESSKAPQQTL | KQGQKRKIQL | D.SSDQLFSQ | 210 |
| ratvac | GLIDEIYGIQ | NSYVK....L | PPEKFAPKKQ | GGGGGKDLP. | ..TEAKKLQL | N.SAEELYAE | 299 |
| slp1_yeast | GLLDDLYEFN | SG........ | .......... | .GMVNSVKVP | IKIKEKDMNE | NYKEDKIWND | 328 |
| slp1_caeel | GLLDEIYGI. | .......... | .......... | .EMEFKNEKDG | DPFQEKEVYL | ...IDEYYHR | 292 |
| | | | | | | |
| hbra | LRDANPAIVG | DILNKVARRL | ETDYESRHTA | KTTTELREFV | NKLPSYQLEH | QSLRVHTNLA | 269 |
| afvac | VRDANFAIVG | DILNKVARRL | ESEYETRHAA | KTASELREFV | NKLPAYQLEH | QSLRVHTNLA | 270 |
| ratvac | TRDKNFNAVG | SVLSKKAKIT | SAAEERHNA | KTVGEIKQFV | SQLPHMQAAR | GSLANHTSIA | 359 |
| slp1_yeast | LKFLNFGSIG | PQLNKIAKEL | QTQYDTRHKA | ESVHEIKEFV | DSLGSLQQRQ | AFLKNHTTLS | 388 |
| slp1_caeel | LKHSHINAVS | IEASKVLAEI | RDDEQFDRDK | MSVAEYSVLV | KKMPKIINRK | KMIEVHMRLA | 352 |
| | | | | | | |
| hbra | EEIMKNTRSD | T...FRKILE | VQQNDAAGAD | PTYQHPLIEE | LIAR...... | D IPLKTILRLL | 321 |
| afvac | QEIMRNTRSD | I...FRKVLE | VQQNNAAGTD | PTYQHDTIEE | LIAR...... | D VPLKTVLRLL | 322 |
| ratvac | ELIKDVTTSE | D...FFDKLT | VEQEFMSGID | TDKVNNYIED | CIAQ......K | HPLIKVLRLV | 411 |
| slp1_yeast | SDVLKVVETE | EYGSFNKILE | .NTLNNDIED | ILELQYQYE | VDQKKILRLI | 445 |
| slp1_caeel | EMI....QSH | VYCKQSDSIK | LERDLLEYSD | SDKAIPLIED | LIFD......A | SPLNAVLRLI | 403 |
| | | | | | | |
| hbra | CLESCMSGGL | RPKDLESFKR | QVVHAYGHQH | LLTFSALEKM | ELLQPRSSAT | TMLIPGTGTQ | 381 |
| afvac | CLESCMSGGL | RSRDLENFKK | QIVHAYGHQH | ILTFSALEKM | ELLQPRSSAA | TMLIPTAGAQ | 382 |
| ratvac | CLQSMCNSGL | KQKVLDYYKR | EILQTYGYEH | ILTLNNLEKA | GLLK......AQ | ..AQ | 457 |
| slp1_yeast | CLLSLCKNSL | REKDYEYLRT | FMIDSWGIEK | CEQLESLAEL | GEETSKTGKT | DLHI.TTSKS | 504 |
| slp1_caeel | SYHSLTCGGL | KPSVLQHYRR | IVNQSYGSSA | LNKVLKMQKM | GLIREKGGGG | KMQCEYA... | 460 |
| | | | | | | |
| hbra | TGSKTNYAYF | RKNLRLVVEE | V......... | SEKEPEDIAY | VYSGFAPLSI | RLVQCVLQKS | 432 |
| afvac | PGTKTNYNYL | RKNLRLLVEE | V......... | SEEDPNDIAY | VYSAFAPLSI | RLVQCVL... | 430 |
| ratvac | TGGRNNYPTI | RKTLRIWMDD | V......... | NEQNPTDISY | VYSGVAPLSV | RLAQLL.... | 504 |
| slp1_yeast | TRLQKEYRYI | SQWENTVPIE | DEHAADKITN | ENDDFSEATE | AYSGVVPLTM | RLVQMLYDRS | 564 |
| slp1_caeel | ...QMMFQQM | KKNHDMLPEE | F......... | SEAKLDDWAY | AYSGFSPLLC | KMLE...... | 502 |

*FIG._2B*

| | | | | | | | |
|---|---|---|---|---|---|---|---|
| hbra | YVMSLMKGGP | AAHANTASPG | WLGYEDVVKS | ARGSTFSIVQ | KGDDKAVRAR | QTLSGNNAAK | 492 |
| afvac | ........ | ........ | ........ | ........ | ........ | ........ | 430 |
| ratvac | ........ | ..SRPG | WRSIEEVLRI | LPGPHFEERQ | PLPTGVQKKR | QP..GENR | 544 |
| slp1_yeast | ILFHNYSSQQ | PFILSREPRV | SQTEDLIEQL | YGDSHAIEES | IWVPGTITKK | INASIKSNNR | 624 |
| slp1_caeel | ........ | ........ | ........ | .EGDRVKWV | GWPKTVIGDK | SDLIAERDGR | 530 |
| | | | | | | | |
| hbra | ........ | .TVYVF | PLGGITFTEI | AALRFIA... | AQEAPRRNIV | ICTTGLINGD | 534 |
| afvac | ........ | ........ | ........ | ........ | ........ | ........ | 430 |
| ratvac | ........ | .VTLVF | FLGGVTFAEI | AALRFLS... | QLEDGGTEYV | IATTKLINGS | 586 |
| slp1_yeast | RSIDGSNGTF | HAAEDIALVV | FLGGVTMGEI | AIMKHLQKIL | GKKGINKRFI | HIADGLINGT | 684 |
| slp1_caeel | ........ | .GTCVF | VIGGLTRSEL | AIIR..... | ..ENLPNVAL | ITTSALITGD | 567 |
| | | | | | | | |
| hbra | RMMDAALEKG | GFALTES | 551 | | | | |
| afvac | ........ | ....... | 430 | | | | |
| ratvac | SWLEALMEKP | F*..... | 597 | | | | |
| slp1_yeast | RIMNSIS.. | ....... | 691 | | | | |
| slp1_caeel | KLLNNITN.. | ....... | 575 | | | | |

FIG._2C

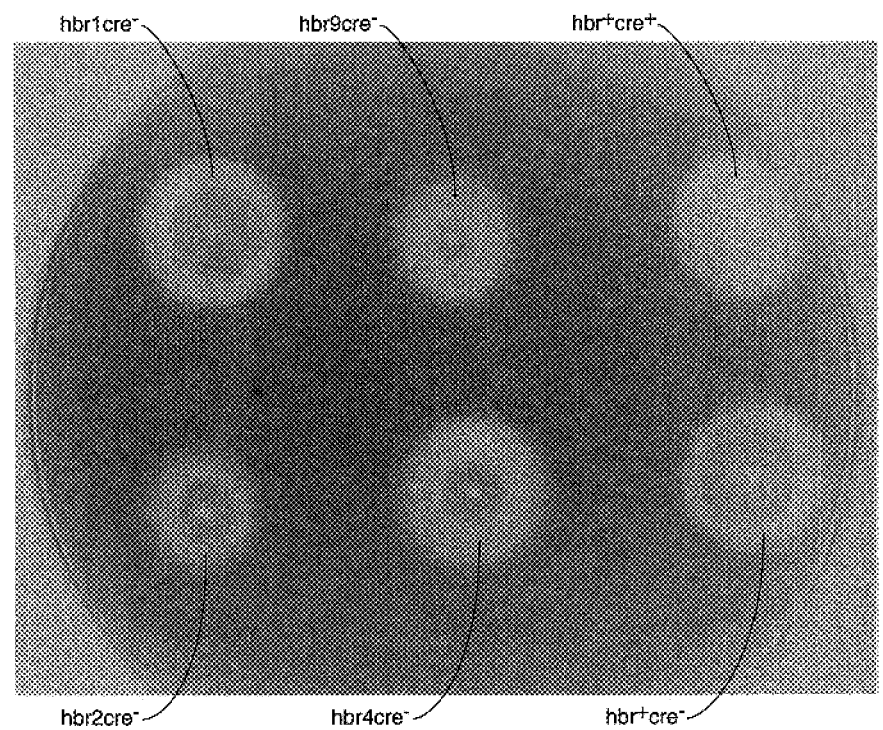

HYPHAL GROWTH IN FUNGI

FIELD OF THE INVENTION

The present invention generally relates to hyphal growth in fungi and in particular describes the modulation of genes associated with hyphal growth in filamentous fungi. The present invention provides methods and systems for the production of proteins and/or chemicals from filamentous fungi which comprise modulation of genes associated with hyphal growth.

BACKGROUND OF THE INVENTION

While the number of fungal species described is approximately 64,000, it is estimated that over one million species exist making this a diverse group of organisms. About 90% of fungi grow in the form of a radiating system of branching hyphae known as the mycelium. This mode of growth reflects a different life style from unitary organisms such as yeasts, with distinct advantages for advancing over surfaces and penetrating substrata (Carlile, 1994, The Growing Fungus, ed. Gow, N. A. R. & Gadd, G. M., Chapman & Hall, pp.3–19). To date very few genes have been characterized which effect fungal branching. The most characterized gene is cot1 isolated from the fungus *Neurospora crassa*. Cot-1 is a temperature sensitive mutation leading to hyperbranching and the sequence, whose function is unknown, appears to encode a cAMP dependent protein kinase (Yarden et al, 1992, EMBO J. 11:2159–2166).

Filamentous fungi find industrial importance as producers of antibiotics, enzymes, fine chemicals and food (*Aspergillus: 50 Years On* (1994) vol 29, ed S. D. Martinelli & J. R. Kinghorn pp. 561–596). There remains a need in the art for improved methods of producing proteins in filamentous fungus. Filamentous fungus are also known pathogens of plants and animals. Therefore, understanding the genetic basis of fungal growth will provide insight regarding possible anti-fungal therapies.

SUMMARY OF THE INVENTION

The present invention is based, in part, upon the discovery of Aspergillus genes that are associated with fungal morphology and in particular with hyphal branching. A linear relationship between the degree of hyphal branching (measured as hyphal growth unit length) and culture viscosity in the fermentor (as measured by torque exerted on the rheometer impeller) has been observed. Isolation of hyper branching fungal mutants and identification of genes associated with fungal hyper branching provides a means for modulating fungal morphology thereby providing a means for controlling viscosity and improving fermentor performance.

The present invention is also based, in part, upon the identification of an *A. nidulans* mutant for the production of HbrA (the mutant being referred to herein as HbrA2) which exhibits a hyperbranching phenotype at the restrictive temperature, 42° C. The mutation HbrA2 does not appear to affect growth of *A. nidulans* at 26° C., but results in a hyperbranching, restricted growth phenotype at 42° C. The HbrA2 mutant comprising the heterologous nucleic acid encoding the *M. meihei* protease was able to secrete the protease at 26° C. The HbrA2 mutant was unable to secrete the protease at 37° C. but was able to secrete the endogenous alpha amylase at temperatures greater than 37° C. The present invention provides the amino acid, HbrA, and nucleic acid sequence for hbrA and methods for producing heterologous protein or chemicals in fungi by modulating the expression of proteins associated with hyphal growth, such as HbrA.

Accordingly, the present invention provides an isolated protein associated with hyphal growth in fungi having at least 70%, at least 75%, at least 80%, at least 85%, at least 90% or at least 95% identity to the amino acid sequence as disclosed in SEQ ID NO:2. In one embodiment, the protein associated with hyphal growth is HbrA which has the amino acid sequence as disclosed in SEQ ID NO:2. The present invention provides polynucleotides encoding the amino acid having the sequence as shown in SEQ ID NO:2 as well as polynucleotides having at least 60%, at least 65%, at least 70%, at least 75%, at least 80%, at least 85%, at least 90% or at least 95% identity to the polynucleotide having the sequence as shown in SEQ ID NO: 1. In one embodiment, the polynucleotide is capable of hybridizing to the polynucleotide having the sequence as shown in SEQ ID NO:1 under conditions of intermediate to high stringency, or is complementary to the polynucleotide having the sequence as shown in SEQ ID NO:1. In another embodiment, the polynucleotide has the nucleic acid sequence as disclosed in SEQ ID NO:1. The present invention also provides host cells and expression vectors comprising a polynucleotide encoding SEQ ID NO:2

In one embodiment, the host cell is a fungus and in another is a filamentous fungus including Aspergillus, Trichoderma, Mucor and Fusarium. In yet a further embodiment, the Aspergillus species includes, but is not limited to, *A. niger, A. nidulans, A. oiyzae* and *A. fumigatus*.

The present invention also provides a method for producing a desired protein in a fungus comprising the step of culturing a recombinant fungus comprising a polynucleotide encoding the desired protein under conditions suitable for the production of said desired protein, said recombinant fungus further comprising a polynucleotide encoding a protein associated with hyphal growth in said fungus said protein associated with hyphal growth having at least 70%, at least 75%, at least 80%, at least 85%, at least 90% or at least 95% identity to the amino acid sequence as disclosed in SEQ ID NO:2. In one embodiment, the polynucleotide encoding a protein associated with hyphal growth is homologous to said fungus and is present in amounts greater than found in the naturally occurring fungus. In another embodiment, the polynucleotide encoding a protein associated with hyphal growth is heterologus to said fungus and has been recombinantly introduced into said fungus. The method may further comprise the step of recovering said desired protein.

In another aspect of the present invention, it may be desirable to down regulate expression of the protein associated with hyphal growth in order to reduce culture viscosity. Accordingly, the present invention provides a method for producing a desired protein in a fungus comprising the step of culturing a recombinant fungus comprising a polynucleotide encoding the desired protein under conditions suitable for the production of said desired protein, said recombinant fungus comprising a mutation in an endogenous nucleic acid encoding a protein associated with hyphal growth said mutation resulting in the inhibition of the production by said fungus of the protein associated with hyphal growth.

In one embodiment, the polynucleotide encoding a protein associated with hyphal growth in said fungus comprises a replicating plasmid. In another embodiment, the polynucleotide encoding a protein associated with hyphal growth in said fungus is integrated into the fungal genome. In yet a further embodiment, the protein associated with hyphal growth has the amino acid sequence as shown in SEQ ID NO:2.

In yet a further embodiment of the present invention, the polynucleotide encoding a protein associated with hyphal growth has at least 60%, at least 65%, at least 70%, at least 75%, at least 80%, at least 85%, at least 90% or at least 95% identity to the polynucleotide having the sequence as shown in SEQ ID NO: 1, or is capable of hybridizing to the polynucleotide having the sequence as shown in SEQ ID NO:1 under conditions of intermediate to high stringency, or is complementary to the polynucleotide having the sequence as shown in SEQ ID NO:1. In another embodiment, the polynucleotide has the nucleic acid sequence as shown in SEQ ID NO: 1.

The present invention also provides a method for producing a recombinant fungus comprising a polynucleotide encoding a protein associated with hyphal growth comprising the steps of obtaining a polynucleotide encoding said protein associated with hyphal growth; introducing said polynucleotide into said host cell; and growing said host cell under conditions suitable for the production of said protein associated with hyphal growth. In one embodiment of this method, the host cell is a fungus. In another embodiment, the filamentous fungus includes Aspergillus, Trichoderma, Mucor and Fusarium species. In yet another embodiment, the Aspergillus species includes *A. niger, A. nidulans, A. oryzae* and *A. fumigatus*. In one embodiment, the polynucleotide has at least 60% identity to the nucleic acid having the sequence as shown in SEQ ID NO:1 or is capable of hybridizing to the polynucleotide having the sequence as shown in SEQ ID NO:1 under conditions of intermediate to high stringency, or is complementary to the polynucleotide having the sequence as shown in SEQ ID NO:1. In another embodiment, the polynucleotide has the sequence as shown in SEQ ID NO:1.

The present invention also relates to methods for screening for mutants exhibiting a hyper branching phenotype and which are capable of secreting heterologous protein. Accordingly, the present invention provides a method for the identification of hyper-branching mutants which comprise the steps of obtaining fungal mutants, subjecting said mutants to selection under desired conditions, and identifying mutants having the desired phenotypes. In one embodiment, the identification comprises selecting for hyphal growth. In yet another embodiment, identification comprises selecting for mutants capable of secreting protein. In another embodiment, the selection comprises growth and/or secretion of heterologous proteins at a restricted temperature.

BRIEF DESCRIPTION OF THE DRAWINGS

FIGS. 1A–1E illustrates the nucleic acid (SEQ ID NO:1, hbrA) and amino acid (SEQ ID NO:2) sequence for HbrA.

FIGS. 2A–2C illustrates an amino acid alignment of the amino acid sequence for hbrA (SEQ ID NO: 2) A. fumigatus (afvac) (SEQ ID NO: 3); rat (ratvac) (SEQ ID NO: 4); yeast sip gene (sip1—yeast) (SEQ ID NO: 5); and *C. elegans* (sip1—cee1).

FIG. 3 illustrates amylase secretion by hbr/creA mutants.

DETAILED DESCRIPTION OF THE INVENTION

Definitions

As used herein, the phrase "protein associated with hyphal growth" refers to a protein which is capable of modulating hyphal growth in fungus. Illustrative of such proteins are the proteins HbrA 1–9 disclosed herein in the Examples. The term "HbrA" refers to the amino acid sequence as shown in SEQ ID NO:2. The present invention encompasses proteins associated with hyphal growth in fungus having at least 70%, at least 75%, at least 80%, at least 85%, at least 90% or at least 95% identity to the amino acid sequence as disclosed in SEQ ID NO:2. Percent identity at the nucleic acid level is determined using the FastA program and percent identity at the amino acid level is determined using the TFastA both of which use the method of Pearson and Lipman (PNAS USA, 1988, 85:2444–2448). The present invention also encompasses mutants, variants and derivatives of HbrA as long as the mutant, variant or derivative is capable of modulating hyphal growth in fungus.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof.

The terms "isolated" or "purified" as used herein refer to a nucleic acid or amino acid that is removed from at least one component with which it is naturally associated.

As used herein, the term "heterologous" when refering to a protein associated with hyphal growth refers to a protein that does not naturally occur in a fungal cell. The term "homologous" when refering to a protein associated with hyphal growth refers to a protein native or naturally occurring in the fungus. The invention includes fungal host cells producing the homologous protein associated with hyphal growth at higher copy number than found in the naturally occurring fungal host and produced at a higher copy level via recombinant DNA technology.

As used herein, the term "overexpressing" when referring to the production of a protein in a host cell means that the protein is produced in greater amounts than its production in its naturally occurring environment.

DESCRIPTION OF THE PREFERRED EMBODIMENTS

The present invention relates to the identification of HbrA in *A. nidulans*. The mutation of HbrA, referred to herein as HbrA2, was assigned to chromosome VII by parasexual analysis (*Aspergillus: 50 Years On* (1994) vol 20, ed S. D. Martinelli & J. R. Kinghorn pp. 41–43). At 37° C., mutant hbrA2, unlike wild-type *A. nidulans*, fails to secrete recombinantly expressed *M. meihei* protease. The translated sequence of the hbrA2 gene shows significant identity with the yeast SLP/VPS33 Sec1 gene product. Available evidence indicates that SLP/VPS33 Sec1 encodes a protein essential for vacuolar protein sorting. SLP1 mutants fail to direct proteins to the vacuoles, and they are sent along a default pathway to the cytoplasmic membrane. The exact nature and function of the SLP1/VPS33 Sec1 protein is unknown, but it is a member of the SEC1 family, and may be a membrane associated protein involved in directing vesicles to vacuoles. Deletion of VPS33 in yeast in not lethal, but leads to slow growth, temperature sensitivity, and loss of vacuoles as revealed by staining light and electron microscopy. Fluorescence microscopy has shown that like SLP1/VSP33 mutants in yeast, HbrA2 is defective in vacuole assembly at the non-permissive temperature.

The mutation HbrA2 does not appear to affect growth of A. nidulans at 26° C., but results in a hyperbranching, restricted growth phenotype at 42° C. The hyperbranching phenotype shows extensive branching in the apical compartment, unlike the wild-type A. nidulans. The mutant grows slowly at the non-permissive temperature giving rise to highly compact colonies on agar media. Mucor meihei protease was transformed into wild-type A. nidulans and crossed into the hbrA2 mutant. The hbrA2 mutant comprising the heterologous nucleic acid encoding the M. meihei protease was able to secrete the protease at 26° C. The hbrA2 mutant was unable to secrete the protease at 37° C. but was able to secrete the endogenous alpha amylase at temperatures greater than 37° C.

In view of the observation that hbrA mutants are incapable of producing foreign protein, it appears that genetically engineering fungal hosts to modulate the expression of proteins associated with hyphal growth, in particular, mutants HbrA1–9, would provide a means for enhancing the production of proteins or chemicals in the fungal host. In one aspect of the present invention, it would be desirable to increase expression of proteins associated with hyphal growth. In another aspect of the present invention, it would be desirable to decrease or eliminate expression of proteins associated with hyphal growth by means known to the skilled artisan.

I. HbrA Amino Acid and hbrA Nucleic Acid Sequences

The present invention provides the amino acid (SEQ ID NO:2) HbrA and nucleic acid (SEQ ID NO:1) sequence for hbrA. The present invention encompasses amino acid variants having at least 70% identity to the amino acid having the sequence as shown in SEQ ID NO:2 as long as the variant is capable of modulating hyphal growth. Percent identity at the nucleic acid level is determined using the FastA program and percent identity at the amino acid level is determined using the TFastA both of which use the method of Pearson and Lipman (PNAS USA, 1988, 85:2444–2448). Alternatively, identity is determined by MegAlign Program from DNAstar (DNASTAR, Inc. Maidson, Wis. 53715) by Jotun Hein Method (1990, Method in Enzymology, 183: 626–645) with a gap penalty=11, a gap length penalty=3 and Pairwise Alignment Parameters Ktuple=2. As the skilled artisan will readily recognize, a variety of polynucleotides can encode HbrA. The present invention encompasses all such polynucleotides. HbrA, and other polynucleotides encoding proteins associated with hyphal growth, may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U. K. Vol. I, II.) Nucleic acid sequences derived from genomic DNA may contain regulatory regions in addition to coding regions. Whatever the source, the isolated polynucleotide encoding the protein associated with hyphal growth can be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the gene may be accomplished in a number of ways. For example, a polynucleotide encoding a protein associated with hyphal growth or its specific RNA, or a fragment thereof, such as a probe or primer, may be isolated and labeled and then used in hybridization assays to detect related genes. (Benton, W. and Davis, R., 1977, Science 196:180; Grunstein, M. And Hogness, D., 1975, Proc. Natl. Acad. Sci. USA 72:3961). Those DNA fragments sharing substantial sequence similarity to the probe will hybridize under stringent conditions.

Also included within the scope of the present invention are fungal microorganism polynucleotide sequences that are capable of hybridizing to the nucleotide sequence of SEQ ID NO:1 under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.) incorporated herein by reference, and confer a defined "stringency" as explained below.

"Maximum stringency" typically occurs at about Tm-5° C. (50° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) Dictionary of Biotechnology, Stockton Press, New York N.Y).

The process of amplification as carried out in polymerase chain reaction (PCR) technologies is described in Dieffenbach CW and GS Dveksler (1995, PCR Primer, a Laboratory Manual, Cold Spring Harbor Press, Plainview N.Y.). A nucleic acid sequence of at least about 10 nucleotides and as many as about 60 nucleotides from SEQ ID NO:1 preferably about 12 to 30 nucleotides, and more preferably about 20–25 nucleotides can be used as a probe or PCR primer.

Expression Systems

The present invention provides host cells, expression methods and systems for the production of desired proteins in host fungus. Once nucleic acid encoding a protein associated with hyphal growth is obtained, recombinant host cells containing the nucleic acid may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989). Nucleic acid encoding proteins associated with hyphal growth and having at least 60% identity to hbrA is obtained and transformed into a host cell using appropriate vectors. A variety of vectors and transformation and expression cassettes suitable for the cloning, transformation and expression in fungus are known by those of skill in the art.

Typically, the vector or cassette contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the protein associated with hyphal growth in a host cell are known to those skilled in the art. Virtually any promoter capable of driving these proteins is suitable for the present invention. Nucleic acid encoding the protein is linked operably through initiation codons to selected expression control regions for effective expression of the protein. Once suitable cassettes are constructed they are used to transform the host cell.

General transformation procedures are taught in Current Protocols In Molecular Biology (vol.1, edited by Ausubel et al., John Wiley & Sons, Inc. 1987, Chapter 9) and include calcium phosphate methods, transformation using PEG and electroporation. For Aspergillus and Trichoderma, PEG and Calcium mediated protoplast transformation can be used (Finkelstein, DB 1992 Transformation. In Biotechnology of Filamentous Fungi. Technology and Products (eds by Finkelstein & Bill) 113–156. Electroporation of protoplast is disclosed in Finkelestein, DB 1992 Transformation. In Biotechnology of Filamentous Fungi. Technology and Products (eds by Finkelstein & Bill) 113–156. Microprojection bombardment on conidia is described in Fungaro et al. (1995) Transformation of *Aspergillus nidulans* by microprojection bombardment on intact conidia. FEMS Microbiology Letters 125 293–298. Agrobacterium mediated transformation is disclosed in Groot et al. (1998) *Agrobacterium tumefaciens*-mediated transformation of filamentous fungi. Nature Biotechnology 16 839–842.

Host cells which comprise the sequence for hbrA and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein. For production of a desired protein in a fungal host cell, an expression vector comprising at least one copy of nucleic acid encoding a desired protein is transformed into the recombinant host cell comprising nucleic acid encoding a protein associated with hyphal growth and cultured under conditions suitable for expression of the protein. Examples of desired proteins include enzymes such as hydrolases including proteases, cellulases, amylases, carbohydrases, and lipases; isomerases such as racemases, epimerases, tautomerases, or mutases; transferases, kinases and phophatases along with proteins of therapeutic value. Alternatively, it may be advantageous to down-regulate or mutate proteins associated with hyphal growth in order to reduce the viscosity in the fermentor.

III Vector Sequences

Expression vectors used in expressing the hprA in fungal cells or the desired protein in fungal cells comprise at least one promoter associated with the protein which promoter is functional in the host cell. In one embodiment of the present invention, the promoter is the wild-type promoter for the protein and in another embodiment of the present invention, the promoter is heterologous to the protein, but is still functional in the fungal host cell. In one preferred embodiment of the present invention, nucleic acid encoding the protein is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the host which allows for ease of selection of those hosts containing the vector.

IV. Assay of the Activity of Proteins Associated with Fungal Growth

The results shown in Examples I and II illustrate the use of a temperature based screen to identify mutants which effect fungal branching. The unexpected advantage of using such a temperature based screen is the ability to identify HbrA mutants or mutants of proteins associated with hyphal growth having a differential effect on the export of native or endogenous genes vs the export of recombinantly introduced heterologous protein. This type of screening method facilitates the isolation of strains which are capable of increased secretion of heterologous protein. Therefore, the present invention also provides a method for the identification of hyper-branching mutants which enhance protein secretion comprising the steps of obtaining fungal mutants, subjecting said mutants to selection under desired conditions, and identifying the desired mutants. In one embodiment, the identification comprises selecting for hyphal growth. In another embodiment, the selection comprises growth and/or secretion of heterologous proteins at a restricted temperature.

EXAMPLES

Example I

This example illustrates the isolation of the hbrA gene. In order to isolate the hbrA gene, DNA was prepared from pooled cosmids of the chromosome-sorted cosmid library of wild-type DNA from *A. nidulans* obtained from FGSC (Funal Genetic Stock Center, Department of Microbiology University of Kansas Medical Center, Kansas City, Kans. 66160). 5 pools of 20 cosmids each were used in transformation experiments. In order to assess transformation efficiency, an hbrA2, argB double mutant was used as a recipient for cotransformation using a mixture of cosmid DNA and transforming vector Arp, which carries the argB gene and a replicating sequence. After transformation, protoplasts were regenerated and selected on medium lacking arginine at 42° C. One of the cosmid pools gave rise to a few strongly growing, normally conidiating colonies in a background of Arg+Hbr– transformants. The pool was subdivided into 4 pools of 5 cosmids, and transformation repeated. A single cosmid was isolated which was able to complement the hbrA2 mutation, restoring wild-type growth. Sub-cloning of the cosmid led to identification of an EcoRI fragment carrying the transforming sequence. The EcoRI/BamHI fragments failed to complement the mutation suggesting that the BamHI site lies within the hbrA gene. The fragment was isolated and subjected to nucleic acid sequencing. The nucleic acid and amino acid sequence for the hbrA gene is shown in FIGS. 1A–1D. Table I shows protease activity for Hbr2, as well as other identified hyper-branching mutants at the permissive and non-permissive temperatures.

TABLE I

| Strain | Mean Protease Activity (units/gram of biomass) at 26 C. | | Mean Protease Activity (units/gram of biomass) at (37 C.) | |
|---|---|---|---|---|
| | 48 hrs | 72 hrs | 48 hrs | 72 hrs |
| Wild-type | 963 +/− 57 | 703 +/− 12 | 380 +/− 44 | 339 +/− 40 |
| HbrA2 | 857 +/− 18 | 1237 +/− 155 | 0 +/− 0 | 0 +/− 0 |
| Hbr3 | 689 +/− 76 | 1194 +/− 234 | 0 +/− 0 | 0 +/− 0 |
| Hbr6 | 0 +/− 0 | 1892 +/− 122 | 0 +/− 0 | 0 +/− 0 |
| Hbr8 | 0 +/− 0 | 2165 +/− 156 | 0 +/− 0 | 487 +/− 10 |

These findings indicate that a previously uncharacterized filamentous fungal gene hbrA plays a role in heterologous protein export.

Example 2

This Example describes the characterization of hyper-branching mutants of A. nidulans. Below is Table II which shows the chromosomal location of the hbr mutants.

| hbr Mutant | Chromosomal location |
|---|---|
| hbr1 | I |
| hbrA2 | VII |
| hbr3 | I |
| hbr4 | III |
| hbr5 | VIII |
| hbr6 | III |
| hbr7 | III |
| hbr8 | I |
| hbr9 | III |

All mutations were recessive and unlinked to each other and represent previously uncharacterized mutations which effect fungal hyperbranching and protein secretion. The ability of hbrA2 mutant to secrete the endogenous protein alpha amylase at 37° C. was examined by growing the hbrA2:creA− double mutant on petri dishes with starch as the sole carbon source (the CreA gene is a negatively acting regulator of carbon catabolism repression. Mutations of CreA (CreA−) causes carbon catabolism derepression of enzymes such as alpha amylase). The hbrA2:creA− double mutant like the hbrA+:creA− was shown to be capable of secreting the endogenous protein alpha amylase, see FIG. 3. These results indicate the hbrA gene unexpectantly plays a role in heterologous protein secretion.

The hbr3 mutant, like the hbrA2 mutant, produces slightly higher M. meihel protease than the wild-type at 26° C. At 37° C., the hbr3 mutant like the hbrA2 mutant does not produce the M. meihei protease. The hbrA2 mutation is located on chromosome VII, the hbr3 mutation is located on chromosome I. These results indicate that the hbr3 gene product also plays a role in heterologous protein export. Therefore, modulation of the expression of the wild-type hbr3 gene product would appear to be advantageous in increasing heterologous protein export.

The hbr6 and hbr8 mutations which are located on chromosomes III and I respectively, produce significantly higher levels of M. meihei protease than the wild-type at 26° C. and would appear to increase the secretion of heterologous protein in a filamentous fungus grown in the temperature range around 26° C. Therefore, modulation of expression of the wildtype hbr6 and hbr8 gene products would also appear to have utility in increasing heterolgous protein export. Mutant versions of the hbr6 and hbr8 genes have no or significantly less M. meihei secretion than the wild-type as shown by Table III.

TABLE III

| Strain | Mean Protease Activity (units/gram of biomass) at 26 C. | | Mean Protease Activity (units/gram of biomass) at (37 C.) | |
|---|---|---|---|---|
| | 48 hrs | 72 hrs | 48 hrs | 72 hrs |
| Wild-type | 963 +/− 57 | 703 +/− 12 | 380 +/− 44 | 339 +/− 40 |
| hbr5 | 46 +/− 60 | 1152 +/− 133 | 533 +/− 53 | 1648 +/− 797 |
| hbr7 | 0 +/− 0 | 1098 +/− 53 | 580 +/− 60 | 1581 +/− 660 |
| hbr4 | 844 +/− 114 | 1688 +/− 67 | 343 +/− 26 | 260 +/− 15 |
| hbr9 | 0 +/− 0 | 268 +/− 16 | 0 +/− 0 | 1562 +/ 641 |

Table II illustrates that M. meihei protease secretion in the hbr5 and hbr7 mutants yields slightly more protease at 26° C. after 72 hours compared to the wild-type, and significantly more protease at 72 hours at 37° C.

The hbr4 mutant produced significantly more M. meihei protease than the wild-type after 72hours at 26° C. but significantly less protease after 72 hours at 37° C. However, the hbr4:creA− double mutant produced significantly higher levels of alpha amylase/unit area fungal colony that the wild-type strain containing only the creA− mutation. These results indicate a significant role for the hbr4 gene product not only in terms of fungal morphology increasing native protein secretion but also a role for this gene product in heterologous protein export.

The hbr9 mutation exhibited poor expression of M. meihei protease at 26° C., but significantly higher levels of M. meihei protease and alpha amylase/unit area fungal colony than the wild-type.

We claim:

1. An isolated protein associated with hyphal growth in fungi having the amino acid sequence as disclosed in SEQ ID NO:2.

* * * * *

SEQUENCE LISTING

<160> NUMBER OF SEQ ID NOS: 6

<210> SEQ ID NO 1
<211> LENGTH: 3000
<212> TYPE: DNA
<213> ORGANISM: Aspergillus nidulans

<400> SEQUENCE: 1
gatcaccagg aattgcgttg cctgatgcat ggttgggagg gccgccgagg tccacgccag      60

-continued

```
gtggtggggg tgctataccg tgctgcgctt ttgccctcgt gtaagggtca gcaggaatcg      120
gtttcgcgta aggattcgct tcggcaggag ggctcttgtt cttcgacctc gatccaaaga      180
gggcgcggcg gttggaggaa tcgtcgtcgc cggcgtctga cgactttttg aggccgaatc      240
gcttcatagc gtattttagc tagaatactt cgccgaaacc agcgtaggaa tattagagtg      300
aaaataataa attgagaggc tatttatgat tgactgagaa ttgaagagag gggaagggaa      360
ggagggaggg gagcgaagat gttaagtgtc aggggagcag cagcggcaaa agtgtcaaga      420
cgctcctgag actcaaaggc agctatgtaa tcatgataca catagttgtg ctgcaattct      480
ggctatcagt gagtatttta ccgtatgatt actcaccaat tcgactccac taagccgaaa      540
gaagctagcg gggatggctg gacccttcta agcctcaact gagggcggtg ccgcagtcaa      600
acgtcaactg ctcccacccc atgcttcgta taaggtagcc atggcaccat tccctgggtc      660
tgatgccgac aatatcaagg acaaggcccg taaaggcttg ctgaatcttc tcgaaggcgt      720
gagtaaggct cctagttggc actgtttctg gttctagcct gattcattac ctcgatctag      780
gtccgtggga agaagaacct ggtgattagc caggggcttg ctgggcccgt cgggcttttt      840
gtcaagtttt cgcagcttca ggagtatggc gtagaccggg tattcttgct tgaaaatgga      900
aatgtcgact cttctcagcg caatgtggta tttctagcgt acgccgaaaa gatccgccag      960
gtgcgggcag tggcaggtat gtcatgatct ttatccacct ttgatttaca tacccaaatg     1020
actgtaaatg cgaaggctcc ttgctatcgc gcttgctggg agcattaaag ttacgcagac     1080
ttcttctcca ctctgcgtaa tcagtcaagc tccctatatt gaaacttcgt ttagcagctt     1140
atccctaagg cttttctttct ctgcctcgta tgactgaatg ccatcagaat aagctgacaa     1200
gttttacaga gcagatccaa aggcttcaac gcaacagcag tatagaccat gaattttcca     1260
tcttttgggt tccaagacgg accctcgtaa gcaataacat cctagagagc gcaggcatca     1320
ttggagatgt gagcatcgct gagctgcctc tttactttt tcctctagag caggacgttc     1380
tttctttgga actggatgac tcttttgcgg acttgtacct ggtgagatct ttctcctgga     1440
gatagtgatc agtgctgatt cattttgtag cacaaggatc ctgggtgcat cttccattcc     1500
gcaaaggctc ttatggctat tcaacagaga catggctatt ttcctcggat agtaggcaaa     1560
ggcgatcatg ctcgacgact cgctgacctc ctgctgcgga tgaggaagga gattgacgca     1620
gaggaaagct caggactgac aggactgtct ttccggggac ttttacccag ctcaagcatt     1680
gagagtttga tcatcattga ccgagaggtg gacttcggca cccctctgct tacacagcta     1740
acgtatgagg gtctcatcga tgagttggta ggaatcaagc acaaccaagc ggacattgat     1800
acgacaattg caggggccag ctcaactccc caggcccagg agtcttccaa agcatctcaa     1860
caggctaagc aaggtcaaaa gcggaagatt cagttggatt cgtctgacca actgttcagt     1920
caactccgtg acgcgaattt tgctatagtc ggcgatatcc tgaataaggt agcacgtcga     1980
ttagaaacag attatgagag ccgtcataca gcaaaaacga caactgaact tcgcgagttt     2040
gtgaataaac taccatcata tcaactcgaa catcaaagct tgagagttca caccaacctc     2100
gctgaggaaa tcatgaaaaa cacgcgctca gacactttcc gcaagatcct cgaagtgcaa     2160
cagaacgacg ctgcaggcgc cgacccaact taccaacatc ctctcattga ggaactcatc     2220
gcccgggata ttccactgaa gacaatcctc cgtttgcttt gtctcgaatc atgcatgtcc     2280
ggtggcctac ggcctaaaga cctcgagagt tttaaacgcc aagtcgtcca cgcatacggg     2340
caccaacacc tgctaacatt cagtgctttg gagaagatgg agcttctcca gccccggtcg     2400
```

```
tctgcaacca caatgctaat tcccggcacg ggcacccaaa cgggatcgaa aacaaactac    2460
gcctactttc gcaaaaatct tcgcctggtc gtcgaagaag ttagcgagaa ggaacctgaa    2520
gatatcgctt atgtctacag cggtttcgcc cctctcagca ttcgccttgt gcagtgcgtc    2580
ttgcagaaat catacgtcat gtcgcttatg aaaggtggcc cggctgcgca cgcgaatacc    2640
gcatccccag gctggcttgg atatgaagat gtggtgaaga gtgcgcgtgg atcgacgttc    2700
agtattgtcc aaaagggcga cgataaagcg gttcgtgcgc ggcagacact gagtggtaac    2760
aatgcggcta agaccgtgta tgtgttcttc ctcggaggga tcacatttac ggaaatcgcg    2820
gcattgcggt tcattgcggc acaggaggcg ccgaggcgaa acattgtgat ttgtactacg    2880
ggaatcatta atggagatcg gatgatggat gctgcgcttg agaagggggg gtttgccttg    2940
actgagtctt gacctcgtag agcgtacagt taatgtcata ggaactatac cgctatccat    3000
```

<210> SEQ ID NO 2
<211> LENGTH: 551
<212> TYPE: PRT
<213> ORGANISM: Aspergillus nidulans

<400> SEQUENCE: 2

```
His Glu Phe Ser Ile Phe Trp Val Pro Arg Thr Leu Val Ser Asn
  1               5                  10                  15

Asn Ile Leu Glu Ser Ala Gly Ile Ile Gly Asp Val Ser Ile Ala Glu
             20                  25                  30

Leu Pro Leu Tyr Phe Phe Pro Leu Glu Gln Asp Val Leu Ser Leu Glu
         35                  40                  45

Leu Asp Asp Ser Phe Ala Asp Leu Tyr Leu His Lys Asp Pro Gly Cys
     50                  55                  60

Ile Phe His Ser Ala Lys Ala Leu Met Ala Ile Gln Gln Arg His Gly
 65                  70                  75                  80

Tyr Phe Pro Arg Ile Val Gly Lys Gly Asp His Ala Arg Arg Leu Ala
                 85                  90                  95

Asp Leu Leu Arg Met Arg Lys Glu Ile Asp Ala Glu Glu Ser Ser
            100                 105                 110

Gly Leu Thr Gly Leu Ser Phe Arg Gly Leu Leu Pro Ser Ser Ser Ile
        115                 120                 125

Glu Ser Leu Ile Ile Ile Asp Arg Glu Val Asp Phe Gly Thr Pro Leu
    130                 135                 140

Leu Thr Gln Leu Thr Tyr Glu Gly Leu Ile Asp Glu Leu Val Gly Ile
145                 150                 155                 160

Lys His Asn Gln Ala Asp Ile Asp Thr Thr Ile Ala Gly Ala Ser Ser
                165                 170                 175

Thr Pro Gln Ala Gln Glu Ser Ser Lys Ala Ser Gln Gln Ala Lys Gln
            180                 185                 190

Gly Gln Lys Arg Lys Ile Gln Leu Asp Ser Ser Asp Gln Leu Phe Ser
        195                 200                 205

Gln Leu Arg Asp Ala Asn Phe Ala Ile Val Gly Asp Ile Leu Asn Lys
    210                 215                 220

Val Ala Arg Arg Leu Glu Thr Asp Tyr Glu Ser Arg His Thr Ala Lys
225                 230                 235                 240

Thr Thr Thr Glu Leu Arg Glu Phe Val Asn Lys Leu Pro Ser Tyr Gln
                245                 250                 255

Leu Glu His Gln Ser Leu Arg Val His Thr Asn Leu Ala Glu Glu Ile
            260                 265                 270
```

```
Met Lys Asn Thr Arg Ser Asp Thr Phe Arg Lys Ile Leu Glu Val Gln
        275                 280                 285

Gln Asn Asp Ala Ala Gly Ala Asp Pro Thr Tyr Gln His Pro Leu Ile
        290                 295                 300

Glu Glu Leu Ile Ala Arg Asp Ile Pro Leu Lys Thr Ile Leu Arg Leu
305                 310                 315                 320

Leu Cys Leu Glu Ser Cys Met Ser Gly Gly Leu Arg Pro Lys Asp Leu
                325                 330                 335

Glu Ser Phe Lys Arg Gln Val Val His Ala Tyr Gly His Gln His Leu
                340                 345                 350

Leu Thr Phe Ser Ala Leu Glu Lys Met Glu Leu Leu Gln Pro Arg Ser
            355                 360                 365

Ser Ala Thr Thr Met Leu Ile Pro Gly Thr Gly Thr Gln Thr Gly Ser
        370                 375                 380

Lys Thr Asn Tyr Ala Tyr Phe Arg Lys Asn Leu Arg Leu Val Val Glu
385                 390                 395                 400

Glu Val Ser Glu Lys Glu Pro Glu Asp Ile Ala Tyr Val Tyr Ser Gly
                405                 410                 415

Phe Ala Pro Leu Ser Ile Arg Leu Val Gln Cys Val Leu Gln Lys Ser
                420                 425                 430

Tyr Val Met Ser Leu Met Lys Gly Gly Pro Ala Ala His Ala Asn Thr
            435                 440                 445

Ala Ser Pro Gly Trp Leu Gly Tyr Glu Asp Val Val Lys Ser Ala Arg
        450                 455                 460

Gly Ser Thr Phe Ser Ile Val Gln Lys Gly Asp Asp Lys Ala Val Arg
465                 470                 475                 480

Ala Arg Gln Thr Leu Ser Gly Asn Asn Ala Ala Lys Thr Val Tyr Val
                485                 490                 495

Phe Phe Leu Gly Gly Ile Thr Phe Thr Glu Ile Ala Ala Leu Arg Phe
                500                 505                 510

Ile Ala Ala Gln Glu Ala Pro Arg Arg Asn Ile Val Ile Cys Thr Thr
            515                 520                 525

Gly Ile Ile Asn Gly Asp Arg Met Met Asp Ala Ala Leu Glu Lys Gly
        530                 535                 540

Gly Phe Ala Leu Thr Glu Ser
545                 550

<210> SEQ ID NO 3
<211> LENGTH: 430
<212> TYPE: PRT
<213> ORGANISM: Aspergillus fumigatus

<400> SEQUENCE: 3

His Glu Phe Ser Ile Phe Trp Leu Pro Arg Arg Thr Phe Val Ser Asn
1               5                   10                  15

Lys Ile Leu Glu Asp Ala Gly Ile Ile Gly Asp Val Asn Ile Phe Glu
            20                  25                  30

Phe Pro Leu Tyr Phe Val Pro Leu Glu Gln Asp Val Leu Ser Leu Glu
        35                  40                  45

Leu Asp Asp Ser Phe Gly Asp Leu Tyr Leu His Lys Asp Pro Gly Cys
    50                  55                  60

Ile Phe Leu Ala Ala Lys Ala Leu Met Asp Ile Gln Gln Arg His Gly
65              70                  75                  80

Tyr Phe Pro Arg Ile Ile Gly Lys Gly Asp His Ala Arg Arg Leu Ala
                85                  90                  95
```

```
Asp Leu Leu Leu Arg Met Arg Lys Glu Leu Asp Ala Glu Glu Ser Ser
            100                 105                 110

Gly Leu Arg Gly Pro Ser Ala Arg Gly Leu Leu Pro Ser Ala Ser Thr
            115                 120                 125

Glu Ser Leu Ile Ile Ile Asp Arg Met Val Asp Phe Gly Thr Pro Leu
            130                 135                 140

Leu Thr Gln Leu Thr Tyr Glu Gly Leu Ile Asp Glu Phe Val Gly Ile
145                 150                 155                 160

Lys Asn Asn Gln Ala Asp Val Asp Thr Ala Ile Val Gly Ala Asn Ser
            165                 170                 175

Val Pro Gln Ala Gln Glu Ser Ser Lys Ala Pro Gln Gln Thr Leu Lys
            180                 185                 190

Gln Gly Gln Lys Arg Lys Ile Gln Leu Asp Ser Ser Asp Gln Leu Phe
            195                 200                 205

Ser Gln Val Arg Asp Ala Asn Phe Ala Ile Val Gly Asp Ile Leu Asn
            210                 215                 220

Lys Val Ala Arg Arg Leu Glu Ser Glu Tyr Glu Thr Arg His Ala Ala
225                 230                 235                 240

Lys Thr Ala Ser Glu Leu Arg Glu Phe Val Asn Lys Leu Pro Ala Tyr
            245                 250                 255

Gln Leu Glu His Gln Ser Leu Arg Val His Thr Asn Leu Ala Gln Glu
            260                 265                 270

Ile Met Arg Asn Thr Arg Ser Asp Ile Phe Arg Lys Val Leu Glu Val
            275                 280                 285

Gln Gln Asn Asn Ala Ala Gly Thr Asp Pro Thr Tyr Gln His Asp Thr
            290                 295                 300

Ile Glu Glu Leu Ile Ala Arg Asp Val Pro Leu Lys Thr Val Leu Arg
305                 310                 315                 320

Leu Leu Cys Leu Glu Ser Cys Met Ser Gly Gly Leu Arg Ser Arg Asp
            325                 330                 335

Leu Glu Asn Phe Lys Lys Gln Ile Val His Ala Tyr Gly His Gln His
            340                 345                 350

Ile Leu Thr Phe Ser Ala Leu Glu Lys Met Glu Leu Leu Gln Pro Arg
            355                 360                 365

Ser Ser Ala Ala Thr Met Leu Ile Pro Thr Ala Gly Ala Gln Pro Gly
            370                 375                 380

Thr Lys Thr Asn Tyr Asn Tyr Leu Arg Lys Asn Leu Arg Leu Leu Val
385                 390                 395                 400

Glu Glu Val Ser Glu Glu Asp Pro Asn Asp Ile Ala Tyr Val Tyr Ser
            405                 410                 415

Ala Phe Ala Pro Leu Ser Ile Arg Leu Val Gln Cys Val Leu
            420                 425                 430

<210> SEQ ID NO 4
<211> LENGTH: 597
<212> TYPE: PRT
<213> ORGANISM: rat

<400> SEQUENCE: 4

Met Ala Ala His Leu Ser Tyr Gly Arg Val Asn Leu Asn Val Leu Arg
1               5                   10                  15

Glu Ala Val Arg Arg Glu Leu Arg Glu Phe Leu Asp Lys Cys Ala Gly
            20                  25                  30

Ser Lys Ala Ile Val Trp Asp Glu Tyr Leu Thr Gly Pro Phe Gly Leu
```

-continued

```
                35                  40                  45
Ile Ala Gln Tyr Ser Leu Leu Lys Glu His Glu Val Glu Lys Met Phe
 50                  55                  60
Thr Leu Lys Gly Ser Arg Leu Pro Ala Ala Asp Val Lys Asn Ile Ile
 65                  70                  75                  80
Phe Leu Val Arg Pro Arg Leu Glu Leu Met Asp Met Ile Ala Glu Asn
                 85                  90                  95
Val Leu Ser Glu Asp Arg Arg Gly Pro Thr Arg Asp Phe His Ile Leu
                100                 105                 110
Phe Val Pro Arg Arg Ser Leu Leu Cys Glu Gln Arg Leu Lys Asp Leu
                115                 120                 125
Gly Val Leu Gly Ser Phe Ile Tyr Arg Glu Tyr Ser Leu Asp Leu
    130                 135                 140
Ile Pro Phe Asp Gly Asp Leu Leu Ser Met Glu Ser Glu Ser Ala Phe
145                 150                 155                 160
Lys Glu Cys Tyr Leu Glu Gly Asp Gln Thr Ser Leu Tyr His Ala Ala
                165                 170                 175
Lys Gly Leu Met Thr Leu Gln Ala Leu Tyr Gly Thr Ile Pro Gln Ile
                180                 185                 190
Phe Gly His Gly Glu Cys Ala Arg Gln Val Ala Asn Met Met Val Arg
                195                 200                 205
Met Lys Arg Glu Phe Thr Gly Ser Gln Asn Ser Val Phe Pro Val Phe
    210                 215                 220
Asp Asn Leu Leu Leu Asp Arg Asn Val Asp Leu Leu Thr Pro Leu
225                 230                 235                 240
Ala Ser Gln Leu Thr Tyr Glu Gly Leu Ile Asp Glu Ile Tyr Gly Ile
                245                 250                 255
Gln Asn Ser Tyr Val Lys Leu Pro Pro Glu Lys Phe Ala Pro Lys Lys
                260                 265                 270
Gln Gly Gly Gly Gly Lys Asp Leu Pro Thr Glu Ala Lys Lys Leu
    275                 280                 285
Gln Leu Asn Ser Ala Glu Glu Leu Tyr Ala Glu Ile Arg Asp Lys Asn
    290                 295                 300
Phe Asn Ala Val Gly Ser Val Leu Ser Lys Lys Ala Lys Ile Ile Ser
305                 310                 315                 320
Ala Ala Phe Glu Glu Arg His Asn Ala Lys Thr Val Gly Glu Ile Lys
                325                 330                 335
Gln Phe Val Ser Gln Leu Pro His Met Gln Ala Ala Arg Gly Ser Leu
                340                 345                 350
Ala Asn His Thr Ser Ile Ala Glu Leu Ile Lys Asp Val Thr Thr Ser
                355                 360                 365
Glu Asp Phe Phe Asp Lys Leu Thr Val Glu Gln Glu Phe Met Ser Gly
    370                 375                 380
Ile Asp Thr Asp Lys Val Asn Asn Tyr Ile Glu Asp Cys Ile Ala Gln
385                 390                 395                 400
Lys His Pro Leu Ile Lys Val Leu Arg Leu Val Cys Leu Gln Ser Met
                405                 410                 415
Cys Asn Ser Gly Leu Lys Gln Lys Val Leu Asp Tyr Tyr Lys Arg Glu
                420                 425                 430
Ile Leu Gln Thr Tyr Gly Tyr Glu His Ile Leu Thr Leu Asn Asn Leu
                435                 440                 445
Glu Lys Ala Gly Leu Leu Lys Ala Gln Thr Gly Gly Arg Asn Asn Tyr
    450                 455                 460
```

```
Pro Thr Ile Arg Lys Thr Leu Arg Leu Trp Met Asp Val Asn Glu
465                 470                 475                 480

Gln Asn Pro Thr Asp Ile Ser Tyr Val Tyr Ser Gly Tyr Ala Pro Leu
            485                 490                 495

Ser Val Arg Leu Ala Gln Leu Leu Ser Arg Pro Gly Trp Arg Ser Ile
            500                 505                 510

Glu Glu Val Leu Arg Ile Leu Pro Gly Pro His Phe Glu Glu Arg Gln
            515                 520                 525

Pro Leu Pro Thr Gly Val Gln Lys Lys Arg Gln Pro Gly Glu Asn Arg
            530                 535                 540

Val Thr Leu Val Phe Phe Leu Gly Val Thr Phe Ala Glu Ile Ala
545                 550                 555                 560

Ala Leu Arg Phe Leu Ser Gln Leu Glu Asp Gly Gly Thr Glu Tyr Val
            565                 570                 575

Ile Ala Thr Thr Lys Leu Ile Asn Gly Ser Ser Trp Leu Glu Ala Leu
            580                 585                 590

Met Glu Lys Pro Phe
        595

<210> SEQ ID NO 5
<211> LENGTH: 691
<212> TYPE: PRT
<213> ORGANISM: yeast

<400> SEQUENCE: 5

Met Asn Arg Phe Trp Asn Thr Lys Lys Phe Ser Leu Thr Asn Ala Asp
1               5                   10                  15

Gly Leu Cys Ala Thr Leu Asn Glu Ile Ser Gln Asn Asp Glu Val Leu
            20                  25                  30

Val Val Gln Pro Ser Val Leu Pro Val Leu Asn Ser Leu Leu Thr Phe
        35                  40                  45

Gln Asp Leu Thr Gln Ser Thr Pro Val Arg Lys Ile Thr Leu Leu Asp
    50                  55                  60

Asp Gln Leu Ser Asp Asp Leu Pro Ser Ala Leu Gly Ser Val Pro Gln
65                  70                  75                  80

Met Asp Leu Ile Phe Leu Ile Asp Val Arg Thr Ser Leu Arg Leu Pro
                85                  90                  95

Pro Gln Leu Leu Asp Ala Ala Gln Lys His Asn Leu Ser Ser Leu His
            100                 105                 110

Ile Ile Tyr Cys Arg Trp Lys Pro Ser Phe Gln Asn Thr Leu Glu Asp
        115                 120                 125

Thr Glu Gln Trp Gln Lys Asp Gly Phe Asp Leu Asn Ser Lys Lys Thr
    130                 135                 140

His Phe Pro Asn Val Ile Glu Ser Gln Leu Lys Glu Leu Ser Asn Glu
145                 150                 155                 160

Tyr Thr Leu Tyr Pro Trp Asp Leu Leu Pro Phe Pro Gln Ile Asp Glu
                165                 170                 175

Asn Val Leu Leu Thr His Ser Leu Tyr Asn Met Glu Asn Val Asn Met
            180                 185                 190

Tyr Tyr Pro Asn Leu Arg Ser Leu Gln Ser Ala Thr Glu Ser Ile Leu
        195                 200                 205

Val Asp Asp Met Val Asn Ser Leu Gln Ser Leu Ile Phe Glu Thr Asn
    210                 215                 220

Ser Ile Ile Thr Asn Val Val Ser Ile Gly Asn Leu Ser Lys Arg Cys
```

-continued

```
            225                 230                 235                 240
Ser His Leu Leu Lys Lys Arg Ile Asp Glu His Gln Thr Glu Asn Asp
                    245                 250                 255
Leu Phe Ile Lys Gly Thr Leu Tyr Gly Glu Arg Thr Asn Cys Gly Leu
                260                 265                 270
Glu Met Asp Leu Ile Ile Leu Glu Arg Asn Thr Asp Pro Ile Thr Pro
            275                 280                 285
Leu Leu Thr Gln Leu Thr Tyr Ala Gly Ile Leu Asp Asp Leu Tyr Glu
        290                 295                 300
Phe Asn Ser Gly Ile Lys Ile Lys Glu Lys Asp Met Asn Phe Asn Tyr
305                 310                 315                 320
Lys Glu Asp Lys Ile Trp Asn Asp Leu Lys Phe Leu Asn Phe Gly Ser
                325                 330                 335
Ile Gly Pro Gln Leu Asn Lys Leu Ala Lys Glu Leu Gln Thr Gln Tyr
            340                 345                 350
Asp Thr Arg His Lys Ala Glu Ser Val His Glu Ile Lys Glu Phe Val
        355                 360                 365
Asp Ser Leu Gly Ser Leu Gln Gln Arg Gln Ala Phe Leu Lys Asn His
    370                 375                 380
Thr Thr Leu Ser Ser Asp Val Leu Lys Val Val Glu Thr Glu Glu Tyr
385                 390                 395                 400
Gly Ser Phe Asn Lys Ile Leu Glu Leu Glu Leu Ile Leu Met Gly
                405                 410                 415
Asn Thr Leu Asn Asn Asp Ile Glu Asp Ile Ile Leu Glu Leu Gln Tyr
            420                 425                 430
Gln Tyr Glu Val Asp Gln Lys Lys Ile Leu Arg Leu Ile Cys Leu Leu
        435                 440                 445
Ser Leu Cys Lys Asn Ser Leu Arg Glu Lys Asp Tyr Glu Tyr Leu Arg
    450                 455                 460
Thr Phe Met Ile Asp Ser Trp Gly Ile Glu Lys Cys Phe Gln Leu Glu
465                 470                 475                 480
Ser Leu Ala Glu Leu Gly Phe Phe Thr Ser Lys Thr Gly Lys Thr Asp
                485                 490                 495
Leu His Ile Thr Thr Ser Lys Ser Thr Arg Leu Gln Lys Glu Tyr Arg
            500                 505                 510
Tyr Ile Ser Gln Trp Phe Asn Thr Val Pro Ile Glu Asp Glu His Ala
        515                 520                 525
Ala Asp Lys Ile Thr Asn Glu Asn Asp Phe Ser Glu Ala Thr Phe
    530                 535                 540
Ala Tyr Ser Gly Val Val Pro Leu Thr Met Arg Leu Val Gln Met Leu
545                 550                 555                 560
Tyr Asp Arg Ser Ile Leu Phe His Asn Tyr Ser Ser Gln Gln Pro Phe
                565                 570                 575
Ile Leu Ser Arg Glu Pro Arg Val Ser Gln Thr Glu Asp Leu Ile Glu
            580                 585                 590
Gln Leu Tyr Gly Asp Ser His Ala Ile Glu Glu Ser Ile Trp Val Pro
        595                 600                 605
Gly Thr Ile Thr Lys Lys Ile Asn Ala Ser Ile Lys Ser Asn Asn Arg
    610                 615                 620
Arg Ser Ile Asp Gly Ser Asn Gly Thr Phe His Ala Ala Glu Asp Ile
625                 630                 635                 640
Ala Leu Val Val Phe Leu Gly Gly Val Thr Met Gly Glu Ile Ala Ile
                645                 650                 655
```

-continued

```
Met Lys His Leu Gln Lys Ile Leu Gly Lys Lys Gly Ile Asn Lys Arg
            660                 665                 670

Phe Ile Ile Ile Ala Asp Gly Leu Ile Asn Gly Thr Arg Ile Met Asn
            675                 680                 685

Ser Ile Ser
    690

<210> SEQ ID NO 6
<211> LENGTH: 575
<212> TYPE: PRT
<213> ORGANISM: Caenorhabditis elegans

<400> SEQUENCE: 6

Met Ala Ala Asn Glu Asp Arg Asp Ala Ala Ile Leu Asn Trp
 1               5                  10                  15

Glu Gly Thr Ser Glu Ile Lys Ser Ala Asn Glu Tyr Ser Arg Asn Leu
            20                  25                  30

Leu Phe Ser Val Leu Asp Ser Leu Asp Gly Asn Lys Thr Ile Val Trp
         35                 40                  45

Asp Arg Asp Arg Ser Val Met His Arg Val Asn Leu Phe Ala Gly Ala
     50                  55                  60

Ser Val Leu Ala Ala His Gly Val Val Ala Asn His Ser Ile Glu Thr
 65                  70                  75                  80

Lys Lys Ser Ala Ser Thr Pro His Val Phe Phe Leu Ala Pro Thr
             85                  90                  95

Met Val Ser Leu Asp Leu Leu Cys Asp Tyr Ile Asp Asn Val Arg Asn
            100                 105                 110

Asp Ser Tyr Trp Glu Arg Leu Glu Ser Val Lys Glu Ile Pro Leu Cys
            115                 120                 125

Trp Leu Pro Arg Asp Gly Glu Cys Leu Ser Leu Ser Ser Pro Gln Ile
    130                 135                 140

Ala Ala Arg Leu Leu Ile Asn Gly Asp Trp Thr His Leu His Lys Cys
145                 150                 155                 160

Ala Val Ala Leu Asn Gln Leu Ile Asp Met Cys Arg Gly Arg Ser Ser
                165                 170                 175

Ser Ser Asn Gln Arg Pro Met Ser Ile Tyr Ala Lys Gly Lys Trp Ala
            180                 185                 190

Ser Asp Val Ala Lys Met Met Gly Lys Ile Arg Asn Ser Ala Glu Ala
        195                 200                 205

Asp Ser Met Thr Lys Asn Leu Asp Pro Ile Glu Gly Leu Leu Lys Ile
    210                 215                 220

Asn Arg Ile Val Leu Ile Asp Arg Trp Met Asp Pro Leu Thr Pro Met
225                 230                 235                 240

Leu Ser Gln Leu Thr Phe Tyr Gly Leu Leu Asp Glu Ile Tyr Gly Ile
                245                 250                 255

Gly Met Val Asn Ser Val Lys Val Pro Glu Met Glu Phe Lys Asn Glu
            260                 265                 270

Lys Asp Gly Asp Pro Phe Gln Glu Lys Glu Val Tyr Leu Ile Asp Glu
        275                 280                 285

Val Tyr His Arg Leu Lys His Ser His Ile Asn Ala Val Ser Ile Glu
    290                 295                 300

Ala Ser Lys Val Leu Ala Glu Ile Arg Asp Asp Glu Gln Phe Asp Arg
305                 310                 315                 320

Asp Lys Met Ser Val Ala Glu Tyr Ser Val Leu Val Lys Lys Met Pro
```

-continued

```
                325                 330                 335
Lys Ile Ile Asn Arg Lys Lys Met Ile Glu Val His Met Arg Leu Ala
            340                 345                 350
Glu Met Ile Gln Ser His Val Tyr Cys Lys Gln Ser Asp Ser Ile Lys
            355                 360                 365
Leu Glu Arg Asp Leu Leu Glu Tyr Ser Asp Ser Asp Lys Ala Ile Pro
            370                 375             380
Leu Ile Glu Asp Leu Ile Phe Asp Ala Ser Pro Leu Asn Ala Val Leu
385                 390                 395                 400
Arg Leu Ile Ser Val His Ser Leu Thr Cys Gly Gly Leu Lys Pro Ser
            405                 410                 415
Val Leu Gln His Tyr Arg Arg Ile Val Asn Gln Ser Tyr Gly Ser Ser
            420                 425                 430
Ala Leu Asn Lys Val Leu Lys Met Gln Lys Met Gly Leu Ile Arg Glu
            435                 440                 445
Lys Gly Gly Gly Lys Met Gln Cys Glu Tyr Ala Gln Met Met Phe
450                 455                 460
Gln Gln Met Lys Lys Asn His Asp Met Leu Pro Glu Glu Phe Ser Glu
465                 470                 475                 480
Ala Lys Leu Asp Asp Met Ala Tyr Ala Tyr Ser Gly Phe Ser Pro Leu
            485                 490                 495
Leu Cys Lys Met Leu Glu Glu Gly Asp Arg Val Lys Trp Val Gly Trp
            500                 505                 510
Pro Lys Thr Val Ile Gly Asp Lys Ser Asp Leu Ile Ala Glu Arg Asp
            515                 520                 525
Gly Arg Gly Thr Cys Val Phe Val Ile Gly Gly Leu Thr Arg Ser Glu
            530                 535                 540
Leu Ala Ile Ile Arg Glu Asn Leu Pro Asn Val Ala Leu Ile Thr Thr
545                 550                 555                 560
Ser Ala Leu Ile Thr Gly Asp Lys Leu Leu Asn Asn Ile Thr Asn
                565                 570                 575
```